United States Patent [19]

Bailey

[11] 4,046,775

[45] Sept. 6, 1977

[54] 4,5-DIHALOPYRROLE-2-CARBOXAMIDES

[75] Inventor: Denis M. Bailey, East Greenbush, N.Y.

[73] Assignee: Sterling Drug Inc., New York, N.Y.

[21] Appl. No.: 583,280

[22] Filed: June 3, 1975

Related U.S. Application Data

[63] Continuation-in-part of Ser. No. 349,973, April 11, 1973, Pat. No. 3,963,480.

[51] Int. Cl.$^2$ .......................................... C07D 207/44
[52] U.S. Cl. ............................. 260/326.2; 260/326.47
[58] Field of Search ........................ 260/326.2, 326.47

[56] References Cited

U.S. PATENT DOCUMENTS

| 2,792,399 | 5/1957 | Ekenstam et al. | 260/326.47 |
|---|---|---|---|
| 3,393,201 | 7/1968 | Preau | 260/326.2 |
| 3,560,523 | 2/1971 | Etienne et al. | 260/326.9 |
| 3,624,081 | 11/1971 | Dickinson et al. | 260/326.47 |

FOREIGN PATENT DOCUMENTS

| 1,965,267 | 12/1968 | Germany | 260/326.2 |
|---|---|---|---|

OTHER PUBLICATIONS

Patai, "The Chemistry of Amides", 1970 pp. 109-112.
Morrison et al., "Organic Chemistry," 1966, pp. 599, 600.

*Primary Examiner*—Donald G. Daus
*Assistant Examiner*—David E. Wheeler
*Attorney, Agent, or Firm*—William G. Webb; B. Woodrow Wyatt

[57] ABSTRACT

4,5-Dihalopyrrole-2-carboxamide derivatives, prepared by reaction of a corresponding 4,5-dihalopyrrole-2-carboxylic acid halide or a corresponding 4,5-dihalopyrrol-2-yl trihalomethyl ketone with an appropriate amine, useful as antibacterial and herbicidal agents.

22 Claims, No Drawings

4,5-DIHALOPYRROLE-2-CARBOXAMIDES

RELATED APPLICATIONS

This is a continuation-in-part of my prior, copending application Ser. No. 349,973, filed Apr. 11, 1973 now U.S. Pat. No. 3,963,480.

BACKGROUND OF THE INVENTION a. Field of the Invention

This invention relates to 4,5-dihalopyrrole-2-carboxamides useful as antibacterial and herbicidal agents.

b. Description of the Prior Art

The compound, 2-carbamyl-4,5-dichloro-1-methylpyrrole, which is unsubstituted on the amide nitrogen atom, is known (Birch et al., *J. Chem. Soc.* 1964, 2641). However, the known compound was obtained as a degradation product as part of a proof of structure of pyoluteorin and is not known to have any other utility except as a laboratory curiosity.

SUMMARY OF THE INVENTION

This invention relates, in a composition of matter aspect, to 4,5-di-X-1-R-2-C(=O)Q-pyrroles where X is chlorine, bromine or iodine; R is hydrogen or lower-alkyl, and Q is an amino group of a nature to be more precisely defined below, which are useful as antibacterial and herbicidal agents.

In a process aspect, the invention relates to a process for preparing the said 4,5-di-X-1-R-2-C(=O)Q-pyrroles which comprises reacting a 4,5-di-X-1-R-pyrrol-2-yl trihalomethyl ketone with an amine H—Q.

DETAILED DESCRIPTION INCLUSIVE OF THE PREFERRED EMBODIMENTS

More specifically, the invention relates to 4,5-dihalopyrrole-2-carboxamides having the formula:

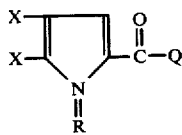

I wherein X is chlorine, bromine or iodine, both values of X being identical; R is hydrogen or lower-alkyl; and Q is benzylamino, 4-morpholino, 1-piperidino, hydrazino, benzylidenehydrazino (or salicyclidenehydrazino), 2-pyridylamino (or lower-alkyl-2-pyridylamino), 2-thiazolylamino, phenylamino, or phenylamino substituted in the phenyl ring by from one to two members of the group consisting of lower-alkoxy, halogen (including fluorine, chlorine, bromine and iodine), loweralkyl, trifluoromethyl, nitro or sulfamoyl, or Q represents a lower-alkylenediamino radical having from two to eight carbon atoms and having its valences on different carbon atoms. When the phenyl ring is substituted by two lower-alkyl or two lower-alkoxy groups on adjacent carbon atoms, the lower-alkyl portion of said moieties is to be understood as being non-tertiary lower-alkyl as further defined below.

As used herein, the term lower-alkyl (or lower-alkoxy) means saturated, monovalent, aliphatic radicals, including straight or branched-chain radicals, of from one to four carbon atoms, as illustrated by, methyl, ethyl, propyl, isopropyl, butyl, sec.-butyl, isobutyl, methoxy, ethoxy, propoxy, isopropoxy, butoxy, sec.-butoxy, isobutoxy, and the like.

The compounds of formula I where R is hydrogen and Q is benzylamino, 4-morpholino, 1-piperidino, hydrazino, phenylamino (or substituted-phenylamino) or lower-alkylenediamino are prepared by reaction of a 4,5-dihalopyrrol-2-yl trihalomethyl ketone with an appropriate amine in an aprotic organic solvent, for example dimethylformamide, benzene, toluene, or xylene. The reaction is normally exothermic and generally goes to completion without application of heat. A preferred solvent is dimethylformamide. The reaction is represented by the following equation, where X and Q have the meanings given above, and X' represents chlorine or fluorine:

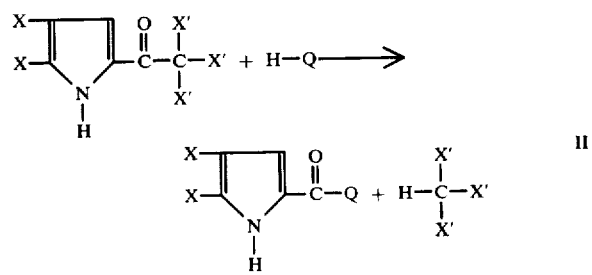

II

The compounds of formula I where R is hydrogen and Q is phenylamino (or substituted-phenylamino), 2-pyridylamino (or lower-alkyl-2-pyridylamino) or 2-thiazolylamino are prepared by reaction of a 4,5-dihalopyrrole-2-carboxylic acid halide of formula III with aniline (or a substituted-aniline), 2-pyridylamine (or lower-alkyl-2-pyridylamine) or 2-aminothiazole. The reaction, represented by the equation:

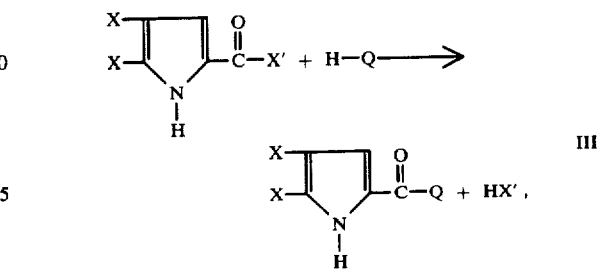

III where Q, X and X' have the meanings given above, is preferably carried out in an aprotic organic solvent, for example benzene, toluene, xylene, methylenedichloride, or ethylenedichloride, and in the presence of a molar excess of pyridine, which serves to take up the hydrogen halide, HX', which is split out during the course of the reaction.

The 4,5-dihalopyrrol-2-yl trihalomethyl ketones of formula II, which are required as intermediates, are described in my copending application Ser. No. 350,086, filed Apr. 11, 1973, and, as disclosed in that application, are prepared by reaction of pyrrole either with a trihaloacetyl halide or with a trihaloacetic anhydride, followed by halogenation of the resulting pyrrol-2-yl trihalomethyl ketone with chlorine or bromine (to prepare the compounds where X is chlorine or bromine) or with iodine monochloride (to prepare the compounds where X is iodine).

The 4,5-dihalopyrrole-2-carboxylic acid halides of formula III are prepared by alkaline saponification of the corresponding 4,5-dihalopyrrol-2-yl trihalomethyl ketones of formula II by warming an aqueous mixture of the ketone and aqueous alkali, isolating the resulting 4,5-dihalopyrrole-2-carboxylic acid from an acid medium, and reaction of the acid with a thionyl halide.

The compounds of formula I where Q is benzylidenehydrazino (or salicylidenehydrazino) are prepared by reacting the corresponding hydrazides (Q is $-NHNH_2$) with benzaldehyde or salicylaldehyde.

The compounds of formula I where R is lower-alkyl are prepared by reacting the corresponding compounds where R is hydrogen with a lower-alkyl halide in an inert organic solvent, for example dimethylformamide, acetone, ethanol, isopropanol, and the like, and in the presence of an acid-acceptor, for example sodium or potassium carbonate. The reaction is advantageously carried out at the reflux temperature of the reaction mixture.

The compounds of formula I have been found to possess antibacterial activity. The antibacterial activity was determined using a modification of the Autotiter method described by Goss et al., Applied Microbiology, 16 (No. 9), 1414–1416 (1968) in which a 1000 mcg./ml. solution of the test compound is prepared. To the first cup of the Autotray is added 0.1 ml. of the test solution. Activation of the Autotiter initiates a sequence of operations by which 0.05 ml. of the test compound solution is withdrawn from this cup by a Microtiter transfer loop and diluted in 0.05 ml. of sterile semi-synthetic medium (glucose). After this operation, 0.05 ml. of inoculated semi-synthetic medium is added automatically to each cup. The overall operation results in final drum concentrations ranging from 500 to 0.06 mcg./ml. in twofold decrements. The Autotray is incubated for 18–20 hours at 37° C., at which time the trays are examined visually for growth as evidenced by turbidity, and the concentration of the last sample in the series showing no growth (or no turbidity) is recorded as the minimal inhibitory concentration (MIC). The compounds of formula I were thus found to be antibacterially effective against *Staphylococcus aureus, Pseudomonas aeruginosa, Escherichia coli*, and *Proteus vulgaris* at concentrations from 2 to 500 mcg./ml.

In standard biological test procedures, certain compounds within the ambit of formula I have also been found to possess herbicidal activity. Specifically, the following compounds of formula I, where R in each instance is hydrogen, have been found to possess post-emergence herbicidal activity.

The compounds are identified by the Example number below where their preparations are described.

| Example | X | Q |
|---|---|---|
| 24 | Cl | $NHCH_2C_6H_5$ |
| 25 | Br | 4-morpholino |
| 28 | Cl | 1-piperidino |
| 1 | Cl | $NHC_6H_5$ |
| 3 | Cl | $NHC_6H_3Cl_2(3,5)$ |
| 5 | Cl | $NHC_6H_4Cl$ (4) |
| 6 | Cl | $NHC_6H_4CH_3(4)$ |
| 7 | Cl | $NHC_6H_4F$ (4) |
| 9 | Br | $NHC_6H_4Br$ (4) |
| 16 | Cl | $NHC_6H_3Cl_2(2,4)$ |

The second above-listed compound where X is Br and Q is 4-morpholino has also been found to possess pre-emergence herbicidal activity. The test procedures used to determine the post and pre-emergence herbicidal activities are described as follows:

Pre-emergence herbicidal activity was determined as follows: Test crop seeds of lima beans, corn, lettuce, mustard and crabgrass were planted in shallow flat-bed trays containing two to three inches of a loam soil, and within twenty-four hours after planting, an aqueous-acetone solution of the test compound was sprayed on the soil at a rate equivalent to 8 pounds of the active ingredient per acre. Test plants were maintained in a greenhouse and watered regularly for two weeks, after which time plant responses were recorded. Individual plant species were examined for percent kill and were rated for overall vigor according to the following scale:

5 — No effect on plants
4 — Slight injury to surviving plants
3 — Moderate injury to surviving plants
2 — Severe injury to surviving plants
1 — Surviving plants are so badly injured they will die.

Plants receiving no chemical treatment were maintained for comparison.

In post-emergence herbicide tests, the test crop seeds were planted as in the pre-emergence test procedure described above, and the growth trays were maintained in a greenhouse and watered regularly for approximately two weeks. When the first trifoliate leaves of bean plants were unfolding, the test plants were removed from the greenhouse and sprayed with an aqueous-acetone solution of the compound being tested at a rate equivalent to 8 pounds of the active ingredient per acre. The plants were maintained in the greenhouse and watered regularly for an additional two weeks after which time the individual plant species were examined for percent kill and rated for overall vigor according to the scale given above. Plants receiving no chemical treatment were maintained for comparison.

The actual determination of the numerical biological data definitive for a particular compound of formula I is readily determined by standard test procedures by technicians versed in biological test procedures, without the need for any extensive experimentation.

When used an antibacterial agents, the compounds of formula I can be formulated for use by preparing a dilute solution in an organic medium in which the compounds are soluble, for example ethyl alcohol or in such solution containing a surfactant, and are applied to a surface to be disinfected by conventional methods such as spraying, swabbing, immersion, and the like. Alternatively, the compounds can be formulated as ointments or creams by incorporating them in conventional ointment or cream bases, for example alkylpolyether alcohols, cetyl alcohol, stearyl alcohol, and the like, or as jellies by incorporating them in conventional jelly bases such as glycerol and tragacanth. They can also be formulated for use as aerosol sprays or foams.

For herbicidal applications, the 4,5-dihalopyrrole-2-carboxamide derivatives of the invention may be utilized in diverse formulations, including agricultural adjuvants and agricultural carriers, i.e. those materials normally employed to facilitate the dispersion of active ingredients in agricultural applications, recognizing the fact that the formulation and mode of application of a toxicant may affect the activity of the material in a given application. Thus, the compounds of this invention may be formulated as granules of relatively large particle size, as wettable powders, as emulsifiable concentrates, as solutions, or as any of several other known types of formulations, depending on the desired mode of application.

Granular formulations are particularly useful for aerial distribution or for penetration of a canopy of foliage. Useful granular formulations may be of several types. Impregnated granules are those wherein the active ingredient is applied to large particles of an absorbent carrier, such as an attapulgite or kaolin clay, corncobs, expanded mica, etc., normally in the form of a solution in a solvent. Surface-coated granules may be produced by spraying the molten active ingredient onto the surface of a generally nonabsorbent particle or by spraying on a solution of active ingredient in a solvent. The core may be water-soluble such as a prilled fertilizer, or insoluble such as sand, marble chips or coarse talc. Particularly useful is a granule wherein a wettable powder is applied as a surface coating to a sand or other insoluble particle such that the wettable may be dispersed on contact of the granule with moisture. Granules may be produced by agglomeration of dusts or powders by compaction rollers, by extrusion through a die or by use of a granulating disc. Granular formulations may vary widely in concentration, with useful formulations containing as little as 0.5 or as much as 95% of active ingredient.

Wettable powders, also useful formulations for both pre- and post-emergence herbicides, are in the form of finely divided particles which disperse readily in water or other dispersants. The wettable powder is ultimately applied to the soil either as a dry dust or as an emulsion in water or other liquid. Typical carriers for wettable powders include fuller's earth, kaolin clays, silicas and other highly absorbent, readily wet inorganic diluents. Wettable powders normally are prepared to contain about 5 to 80% of active ingredient, depending on the absorbency of the carrier, and usually also contain a small amount of a wetting, dispersing or emulsifying agent to facilitate dispersion. For example, a useful wettable powder formulation contains 80.8 parts of a 4,5-dihalopyrrole-2-carboxamide derivative of the invention, 17.9 parts of palmetto clay, and 1.0 part of sodium lignosulfonate and 0.3 part of a sulfonated aliphatic polyester as wetting agents.

Other useful formulations for herbicidal applications are emulsifiable concentrates, which are homogeneous liquid or paste compositions dispersible in water or other dispersant, and may consist entirely of a compound of the invention with a liquid or solid emulsifying agent, or may also contain an agriculturally acceptable liquid carrier, such as xylene, heavy aromatic naphthas, isophorone and other nonvolatile organic solvents.

Typical wetting, dispersing or emulsifying agents used in agricultural formulations include, for example, the alkyl and alkylaryl sulfonates and sulfates and their sodium salts; polyethylene oxides; sulfonated oils, fatty acid esters of polyhydric alcohols; and other types of surface-active agents, many of which are available in commerce. The surface-active agent, when used, normally comprises from 1 to 15% by weight of the herbicidal composition.

These formulations may be applied without further dilution or as dilute solutions, emulsions or suspensions in water or other suitable diluent. The compositions may be applied to the area wherein control is desired by spraying onto the undesired vegetation or onto the surface of the soil in the case of liquid compositions or by distribution from mechanical equipment in the case of solids. The surface-applied material may also be blended into the upper layer of soil by cultivation, or left as applied, as is appropriate to gain the optimum results with the particular treatment.

The active herbicidal compounds of this invention may be formulated and/or applied with insecticides, fungicides, nematicides, plant-growth regulators, fertilizers, and other agricultural chemicals. In applying the active compounds of the invention, whether formulated alone or with other agricultural chemicals, an effective amount and concentration of a 4,5-dihalopyrrole-2-carboxamide derivative of the invention are of course employed.

The molecular structures of the compounds of the invention were assigned on the basis of study of their infrared, ultraviolet, and NMR spectra, and confirmed by the correspondence between calculated and found values for elementary analyses for the elements.

The following examples will further illustrate the invention without, however, limiting it thereto. All melting points are uncorrected.

EXAMPLE 1

A solution of 6.7 g. (0.1 mole) of pyrrole in 70 ml. of diethyl ether was added slowly and with vigorous stirring to a solution of 20 g. (0.11 mole) of trichloroacetyl chloride in 20 ml. of diethyl ether. When addition was complete, stirring was continued for another half hour, and the solution then treated cautiously with an excess of 10% aqueous potassium carbonate. When frothing had subsided, the organic layer was separated, dried, taken to dryness in vacuo, and the residual solid recrystallized with charcoaling from hexane to give 10.2 g. of pyrrol-2-yl trichloromethyl ketone, m.p. 74°-75° C.

Chlorine was bubbled into 450 ml. of glacial acetic acid until a total of 15.6 g. (0.22 mole) had been taken up. This solution was then added slowly and with vigorous stirring to a solution of 22.3 g. (0.11 mole) of pyrrol-2-yl trichloromethyl ketone in 50 ml. of glacial acetic acid. The mixture was stirred for two hours, concentrated to a small volume, treated cautiously with 10% aqueous potassium carbonate, and the mixture extracted with diethyl ether. The combined ether extracts, on drying and concentration, afforded a solid residue which was recrystallized from hexane to give 20.2 g. of 4,5-dichloropyrrol-2-yl trichloromethyl ketone, m.p. 129°-131° C.

A mixture of 21 g. (0.075 mole) of 4,5-dichloropyrrol-2-yl trichloromethyl ketone, 11 g. (0.12 mole) of aniline and 2 g. of lithium chloride in 25 ml. of dimethylformamide was heated for about 8 hours on a steam bath, then diluted with 150 ml. of water and acidified with concentrated hydrochloric acid. The solid which separated was collected and recrystallized, with charcoaling, from a diethyl ether/hexane mixture to give 11.4 g. of 4,5-dichloropyrrole-2-carboxanilide, m.p. 213°-215° C.

EXAMPLE 2

A mixture of 20 g. (0.07 mole) of 4,5-dichloropyrrol-2-yl trichloromethyl ketone (described above in Example 1), 13.2 g. (0.11 mole) of 4-methoxyaniline and 3 g. (0.07 mole) of lithium chloride in 25 ml. of dimethylformamide was heated on a steam bath for about 16 hours and the mixture worked up in the manner described above in Example 1. The product was recrystallized from dilute ethanol to give 9.8 g. of 4,5-dichloro-4'-methoxypyrrole-2-carboxanilide, m.p. 224°-226° C.

By substituting for the 4-methoxyaniline used in the above procedure a molar equivalent amount of 3,4- dimethoxyaniline, 4-ethoxyaniline, 3-isopropoxyaniline, 3-butoxyaniline, or 4-t-butoxyaniline, there can be obtained, respectively, 4,5-dichloro-3',4'-dimethoxypyrrole-2-carboxanilide; 4,5-dichloro-4'-ethoxypyrrole-2-carboxanilide; 4,5-dichloro-3'-isopropoxypyrrole-2-carboxanilide; 4,5-dichloro-3'-butoxypyrrole-2-carboxanilide; or 4-5-dichloro-4'-t-butoxypyrrole-2-carboxanilide.

EXAMPLE 3

A mixture of 68 g. (0.24 mole) of 4,5-dichloropyrrol-2-yl trichloromethyl ketone (described above in Example 1), 115 ml. of 10% aqueous sodium hydroxide and 150 ml. of water was shaken until all solid had dissolved. The mixture was then acidified with concentrated hydrochloric acid, cooled and extracted with diethyl ether. The combined organic extracts were dried over sodium sulfate, charcoaled, concentrated to a volume of about 100 ml., diluted with 200 ml. of hexane, and cooled. The precipitate which separated was collected to give 27.5 g. of 4,5-dichloropyrrole-2-carboxylic acid, m.p. 172°-174° C. A second crop of 6.8 g. of product, m.p. 163°-165° C., was recovered from the filtrate.

A mixture of 12 g. (0.067 mole) of 4,5-dichloropyrrole-2-carboxylic acid and 20 ml. of thionyl chloride was heated under reflux on a steam bath for about 10 minutes, and then cooled and concentrated in vacuo. The residual material was dissolved in 25 ml. of benzene and added slowly and with vigorous stirring to a solution of 11 g. (0.068 mole) of 3,5-dichloroaniline in 75 ml. of pyridine. The mixture was stirred at room temperature for about 48 hours, evaporated to dryness, and the residue partitioned between saturated aqueous sodium bicarbonate solution and diethyl ether. The organic extracts were washed with 125 ml. of dilute hydrochloric acid, dried, charcoaled, and taken to dryness leaving a solid residue which was recrystallized from dilute ethanol to give 12.5 g. of 3',4,5,5'-tetrachloropyrrole-2-carboxanilide, m.p. 234°-235° C.

EXAMPLE 4

4,5-Dichloropyrrole-2-carboxylic acid (18 g., 0.10 mole) was converted to the acid chloride by reaction with 30 ml. of thionyl chloride, and the acid chloride dissolved in 30 ml. of benzene was reacted with 12.8 g. (0.10 mole) of 3-chloroaniline in 75 ml. of pyridine using the procedure described above in Example 3. The crude product was recrystallized from dilute ethanol to give 19.3 g. of 3',4,5-trichloropyrrole-2-carboxanilide, m.p. 247°-249° C.

By substituting for the 3-chloroaniline used in the above procedure a molar equivalent amount of 4-iodoaniline, there can be obtained 4,5-dichloro-4'-iodopyrrole-2-carboxanilide.

EXAMPLE 5

4,5-Dichloropyrrole-2-carboxylic acid (18 g., 0.10 mole) was converted to the acid chloride by reaction with 30 ml. of thionyl chloride, and the acid chloride dissolved in 30 ml. of benzene was reacted with 12.8 g. (0.10 mole) of 4-chloroaniline in 75 ml. of pyridine using the procedure described above in Example 3. The crude product was recrystallized from dilute ethanol to give 20.7 g. of 4,4',5-trichloropyrrole-2-carboxanilide, m.p. 256°-258° C.

EXAMPLE 6

4,5-Dichloropyrrole-2-carboxylic acid (18 g., 0.10 mole) was converted to the corresponding acid chloride by reaction with 30 ml. of thionyl chloride and the acid chloride dissolved in 30 ml. of benzene was reacted with 10.8 g. (0.10 mole) of 4-methylaniline in 75 ml. of pyridine using the procedure described above in Example 3. The crude product was recrystallized from dilute ethanol to give 14.8 g. of 4,5-dichloro-4'-methylpyrrole-2-carboxanilide, m.p. 227°-229° C.

By substituting for the 4-methylaniline used in the above procedure a molar equivalent amount of 3,4-dimethylaniline, 4-ethylaniline, 3-isopropylaniline, or 4-t-butylaniline, there can be obtained, respectively, 4,5-dichloro-3',4'-dimethylpyrrole-2-carboxanilide; 4,5-dichloro-4'-ethylpyrrole-2-carboxanilide; 4,5-dichloro-3'-isopropylpyrrole-2-carboxanilide; or 4,5-dichloro-4'-t-butylpyrrole-2-carboxanilide.

EXAMPLE 7

4,5-Dichloropyrrole-2-carboxylic acid (12 g., 0.067 mole) was converted to the acid chloride by reaction with 20 ml. of thionyl chloride, and the acid chloride dissolved in 25 ml. of benzene was reacted with 75 g. (0.067 mole) of 4-fluoroaniline in 50 ml. of pyridine using the procedure described above in Example 3. The crude product was recrystallized from dilute ethanol to give 14.2 g. of 4,5-dichloro-4'-fluoropyrrole-2-carboxanilide, m.p. 227°-228° C.

EXAMPLE 8

A solution of 10.7 g. (0.05 mole) of pyrrol-2-yl trichloromethyl ketone (described above in Example 1) in 25 ml. of glacial acetic acid was treated slowly and with vigorous stirring with a solution of 16 g. (0.1 mole) of bromine in 25 ml. of glacial acetic acid. When addition was complete, the reaction mixture was warmed at about 50° C. on a water bath for about 15 minutes until the orange bromine color had disappeared. The reaction mixture was then worked up using the procedure described above in Example 1, and the crude product thus obtained recrystallized from hexane to give 15.5 g. of 4,5-dibromopyrrol-2-yl trichloromethyl ketone, m.p. 136°-138° C.

A mixture of 74 g. (0.2 mole) of 4,5-dibromopyrrol-2-yl trichloromethyl ketone in 100 ml. of 10% aqueous sodium hydroxide and 150 ml. of water was heated and stirred on a steam bath for about 10 minutes until all solid had dissolved. The reaction was worked up using the procedure described above in Example 3, and the product recrystallized from a diethyl ether/hexane mixture to give 45 g. of 4,5-dibromopyrrole-2-carboxylic acid, m.p. >160° C. (dec.).

The above 4,5-dibromopyrrole-2-carboxylic acid (13.0 g., 0.048 mole) was converted to the corresponding acid chloride by reaction with 20 ml. of thionyl chloride, and the acid chloride dissolved in 25 ml. of benzene was reacted with 8.1 g. (0.047 mole) of 3-bromoaniline in 50 ml. of pyridine using the procedure described above in Example 3. The product was recrystallized from dilute ethanol to give 17.2 g. of 3',4,5-tribromopyrrole-2-carboxanilide, m.p. 210°-211° C.

EXAMPLE 9

4,5-Dibromopyrrole-2-carboxylic acid (13.0 g., 0.048 mole) was converted to the corresponding acid chloride by reaction with 20 ml. of thionyl chloride, and the acid chloride dissolved in 25 ml. of benzene was reacted with 8.1 g. (0.047 mole) of 4-bromoaniline in 50 ml. of pyridine using the procedure described above in Example 3. The product was recrystallized from dilute ethanol to give 15.5 g. of 4,4′,5-tribromopyrrole-2-carboxanilide, m.p. 243°–245° C.

EXAMPLE 10

4,5-Dibromopyrrole-2-carboxylic acid (13 g., 0.048 mole) was converted to the corresponding acid chloride by reaction with 20 ml. of thionyl cloride, and the acid chloride dissolved in 25 ml. of benzene was reacted with 6.1 g. (0.048 mole) of 4-chloroaniline in 50 ml. of pyridine using the procedure described above in Example 3. The product was recrystallized from dilute ethanol to give 15.8 g. of 4,5-dibromo-4′-chloropyrrole-2-carboxanilide, m.p. 235°–237° C.

EXAMPLE 11

4,5-Dichloropyrrole-2-carboxylic acid (10 g., 0.056 mole) was converted to the corresponding acid chloride by reaction with 15 ml. of thionyl chloride, and the acid chloride dissolved in 25 ml. of benzene was reacted with 9.2 g. (0.057 mole) of 3,4-dichloroaniline in excess pyridine using the procedure described above in Example 3. The product was recrystallized from dilute ethanol to give 14.0 g. of 3′,4,4′,5-tetrachloropyrrole-2-carboxanilide, m.p. 261°–263° C.

EXAMPLE 12

4,5-Dichloropyrrole-2-carboxylic acid (10.0 g., 0.056 mole) was converted to the corresponding acid chloride by reaction with 15 ml. of thionyl chloride, and the acid chloride dissolved in 25 ml. of benzene was reacted with 9.2 g. (0.057 mole) of 2,6-dichloroaniline in 50 ml. of pyridine using the procedure described above in Example 3. The product was recrystallized from a diethyl ether/hexane mixture to give 5.5 g. of 2′,4,5,6′-tetrachloropyrrole-2-carboxanilide, m.p. 212°–214° C.

EXAMPLE 13

4,5-Dibromopyrrole-2-carboxylic acid (10 g., 0.037 mole) was converted to the corresponding acid chloride by reaction with 15 ml. of thionyl chloride, and the acid chloride dissolved in 25 ml. of benzene was reacted with 6 g. (0.037 mole) of 3,5-dichloroaniline in 50 ml. of pyridine using the procedure described above in Example 3. The product was recrystallized from dilute ethanol to give 12.5 g. of 4,5-dibromo-3′,5′-dichloropyrrole-2-carboxanilide, m.p. 245°–248° C.

EXAMPLE 14

4,5-Dibromopyrrole-2-carboxylic acid (10.0 g., 0.037 mole) was coverted to the corresponding acid chloride by reaction with 15 ml. of thionyl chloride, and the acid chloride dissolved in 25 ml. of benzene was reacted with 8.6 g. (0.037 mole) of 3,5-bis(trifluoromethyl)aniline in 50 ml. of pyridine using the procedure described above in Example 3. The product was recrystallized from a diethyl ether/hexane mixture to give 10.4 g. of 4,5-dibromo-3′,5′-bis(trifluoromethyl)pyrrole-2-carboxanilide, m.p. 197°–199° C.

EXAMPLE 15

4,5-Dibromopyrrole-2-carboxylic acid (10 g., 0.037 mole) was converted to the corresponding acid chloride by reaction with 15 ml. of thionyl chloride, and the acid chloride dissolved in 25 ml. of benzene was reacted with 9.4 g. (0.037 mole) of 3,5-dibromoaniline in 50 ml. of pyridine using the procedure described above in Example 3. The product was recrystallized from an ethyl acetate/ethanol mixture to give 14.5 g. of 3′,4,5,5′-tetrabromopyrrole-2-carboxanilide, m.p. 244°–245° C.

EXAMPLE 16

4,5-Dichloropyrrole-2-carboxylic acid (10 g., 0.056 mole) was converted to the corresponding acid chloride by reaction with 15 ml. of thionyl chloride, and the acid chloride dissolved in 25 ml. of benzene was reacted with 9.2 g. (0.057 mole) of 2,5-dichloroaniline in 50 ml. of pyridine using the procedure described above in Example 3. The product was recrystallized from an ethyl acetate/ethanol mixture to give 10.0 g. of 2′,4,4′,5-tetrachloropyrrole-2-carboxanilide, m.p. 262°–264° C.

EXAMPLE 17

4,5-Dibromopyrrole-2-carboxylic acid (10 g., 0.037 mole) was converted to the corresponding acid chloride by reaction with 15 ml. of thionyl chloride, and the acid chloride dissolved in 25 ml. of benzene was reacted with 9.4 g. (0.037 mole) of 2,4-dibromoaniline in 50 ml. of pyridine using the procedure described above in Example 3. The product was recrystallized from dilute aqueous dimethylformamide to give 7.4 g. of 2′,4,4′,5-tetrabromopyrrole-2-carboxanilide, m.p. 272°–275° C.

EXAMPLE 18

4,5-Dichloropyrrole-2-carboxylic acid (10.0 g., 0.056 mole) was converted to the corresponding acid chloride by reaction with 15 ml. of thionyl chloride, and the acid chloride dissolved in 25 ml. of benzene was reacted with 9.2 g. (0.056 mole) of 2,3-dichloroaniline in 50 ml. of pyridine using the procedure described above in Example 3. The product was recrystallized from dilute aqueous dimethylformamide to give 7.9 g. of 2′,3′,4,5-tetrachloropyrrole-2-carboxanilide, m.p. 259°–261° C.

EXAMPLE 19

4,5-Dibromopyrrole-2-carboxylic acid (10.0 g., 0.037 mole) was converted to the corresponding acid chloride by reaction with 15 ml. of thionyl chloride, and the acid chloride dissolved in 25 ml. of benzene was reacted with 6.4 g. (0.037 mole) of 4-sulfamoylaniline in 50 ml. of pyridine using the procedure described above in Example 3. The product was recrystallized from a dimethylformamide/ethanol mixture to give 12.7 g. of 4,5-dibromo-4′-sulfamoylpyrrole-2-carboxanilide, m.p. 267°–268° C.

EXAMPLE 20

4,5-Dichloropyrrole-2-carboxylic acid (20.0 g., 0.11 mole) was converted to the corresponding acid chloride by reaction with 30 ml. of thionyl chloride, and the acid chloride dissolved in 35 ml. of benzene was reacted with 14.2 g. (0.11 mole) of 2-chloroaniline in 75 ml. of pyridine using the procedure described above in Example 3. The product was recrystallized from ethyl acetate to give two crops totaling 23.4 g. of 2′,4,5-trichloropyrrole-2-carboxanilide, m.p. 231°–233° C.

EXAMPLE 21

4,5-Dichloropyrrole-2-carboxylic acid (10 g., 0.06 mole) was converted to the corresponding acid chloride by reaction with 15 ml. of thionyl chloride, and the acid chloride dissolved in 25 ml. of benzene was reacted with 9.2 g. (0.057 mole) of 2,5-dichloroaniline in 50 ml.

of pyridine using the procedure described above in Example 3. The product was recrystallized from pyridine to give two crops totaling 7.4 g. of 2',4,5,5'-tetrachloropyrrole-2-carboxanilide, m.p. 245°-247° C.

EXAMPLE 22

A solution of 21.3 g. (0.10 mole) of pyrrol-2-yl trichloromethyl ketone (described above in Example 1) in 200 ml. of glacial acetic acid was heated on a steam bath and treated slowly and with stirring with 100 ml. of a 2.07N solution of sodium chloride/iodine monochloride in water. When addition was complete, the mixture was stirred and heated for an additional hour and a half, concentrated to a small volume, and treated with an excess of a saturated aqueous sodium bicarbonate solution. The mixture was extracted with diethyl ether, the combined ether extracts dried, charcoaled and concentrated to dryness, and the residual solid recrystallized twice from a diethyl ether/hexane mixture to give 17.2 g. of 4,5-diiodopyrrol-2-yl trichloromethyl ketone, m.p. 176°-177° C.

A mixture of 90 g. (0.19 mole) of 4,5-diiodopyrrol-2-yl trichloromethyl ketone in 50 ml. of 10% sodium hydroxide and 100 ml. of water was heated on a steam bath for about 15 minutes and then acidified with concentrated hydrochloric acid. The product was isolated in the manner described above in Example 3, and the product was recrystallized from a diethyl ether/hexane mixture to give two crops totaling 55.6 g. of 4,5-diiodopyrrole-2-carboxylic acid, m.p. 190°-203° C.

The above 4,5-diiodopyrrole-2-carboxylic acid (11.7 g., 0.032 mole) was converted to the corresponding acid chloride by reaction with 15 ml. of thionyl chloride, and the acid chloride dissolved in 25 ml. of benzene was reacted with 5.2 g. (0.032 mole) of 3,5-dichloroaniline in 50 ml. of pyridine using the procedure described above in Example 3. The product was recrystallized twice from a diethyl ether/hexane mixture to give 3.95 g. of 3',5'-dichloro-4,5-diiodopyrrole-2-carboxanilide, m.p. 237°-240° C.

EXAMPLE 23

A mixture of 10 g. (0.02 mole) of 4,5-dibromo-4'-chloropyrrole-2-carboxanilide (described above in Example 10), 5.7 g. (0.04 mole) of methyl iodide and 12.2 g. (0.09 mole) of potassium carbonate in 100 ml. of acetone was heated under reflux for about an hour and a half. The mixture was then concentrated to a small volume, diluted with 200 ml. of water, and the solid which separated was collected and recrystallized from dilute ethanol to give two crops totaling 9.5 g. of 4,5-dibromo-4'-chloro-1-methylpyrrole-2-carboxanilide, m.p. 200°-202° C.

By replacing the methyl iodide used in the abovedescribed procedure with a molar equivalent amount of ethyl iodide, propyl iodide, isopropyl iodide, butyl iodide, sec.-butyl iodide, or isobutyl iodide, there can be obtained, respectively, 4,5-dibromo-4'-chloro-1-ethylpyrrole-2-carboxanilide; 4,5-dibromo-4'-chloro-1-propylpyrrole-2-carboxanilide; 4,5-dibromo-4'-chloro-1-isopropylpyrrole-2-carboxanilide; 4,5-dibromo-4'-chloro-1-butylpyrrole-2-carboxanilide; 4,5-dibromo-4'-chloro-1-sec.-butylpyrrole-2-carboxanilide; or 4,5-dibromo-4'-chloro-1-isobutylpyrrole-2-carboxanilide.

EXAMPLE 24

A mixture of 22 g. (0.078 mole) of 4,5-dichloropyrrol-2-yl trichloromethyl ketone (described above in Example 1) and 8.3 g. (0.078 mole) of benzylamine in 25 ml. of dimethylformamide was allowed to stand for 45 minutes, diluted with 200 ml. of water and extracted with diethyl ether. The combined extracts were washed with water, dried over sodium sulfate, evaporated to dryness, and the residue recrystallized from anhydrous ethanol to give 12.6 g. of N-benzyl-4,5-dichloropyrrole-2-carboxamide, m.p. 183°-185° C.

EXAMPLE 25

To a solution of 21 g. (0.057 mole) of 4,5-dibromopyrrol-2-yl trichloromethyl ketone (described above in Example 8) in 25 ml. of dimethylformamide was added 10 g. (0.12 mole) of morpholine, and the mixture was allowed to stand for about 12 hours. The reaction was worked up using the procedure described above in Examples 1 and 24, and the product recrystallized from absolute ethanol to give 15.8 g. of 4-[(4,5-dibromopyrrol-2-yl)carbonyl]morpholine, m.p. 198°-200° C.

EXAMPLE 26

A mixture of 25 g. (0.09 mole) of 4,5-dichloropyrrol-2-yl trichloromethyl ketone (described above in Example 1) and 25 ml. of morpholine in 50 ml. of dimethylformamide was allowed to stand for about 12 hours, and the mixture then diluted with water and worked up in the manner described above in Examples 1 and 24. The product was recrystallized from ethanol to give 15.3 g. of 4-[(4,5-dichloropyrrol-2yl)carbonyl]morpholine, m.p. 165°-169° C.

EXAMPLE 27

A mixture of 21 g. (0.057 mole) of 4,5-dibromopyrrol-2-yl trichloromethyl ketone (described above in Example 8) and 10 g. (0.12 mole) of piperidine in 25 ml. of dimethylformamide was allowed to stand for about 12 hours and the mixture then diluted with water and worked up in the manner described above in Examples 1 and 24. The product was recrystallized from absolute ethanol to give 9.8 g. of 1-[(4,5-dibromopyrrol-2-yl)carbonyl]piperidine, m.p. 174°-176° C.

EXAMPLE 28

A mixture of 23 g. (0.082 mole) of 4,5-dichloropyrrol-2-yl trichloromethyl ketone (described above in Example 1) and 13.8 g. (0.16 mole) of piperidine in 25 ml. of dimethylformamide was prepared, allowed to stand for about 12 hours and then diluted with water and worked up in the manner described above in Examples 1 and 24. The product was recrystallized from absolute ethanol to give two crops totaling 10.3 g. of 1-[(4,5-dichloropyrrol-2-yl)carbonyl]piperidine, m.p. 183°-185° C.

EXAMPLE 29

A mixture of 50 g. (0.14 mole) of 4,5-dibromopyrrol-2-yl trichloromethyl ketone (described above in Example 1) and 10 g. (0.30 mole) of 95% hydrazine hydrate in 25 ml. of dimethylformamide was stirred at room temperature for about thirty minutes, diluted with 200 ml. of water, and the solid which separated was collected and washed with water to give 34 g. of 4,5-dibromopyrrole-2-carboxylic acid hydrazide, m.p. 213°-214° C.

EXAMPLE 30

A mixture of 7.0 g. (0.03 mole) of 4,5-dibromopyrrole-2-carboxylic acid hydrazide (described above in Example 29) and 3.1 g. (0.03 mole) of salicylaldehyde in 25 ml. of dimethylformamide containing five drops of glacial acetic acid was heated on a steam bath for about thirty minutes, filtered, cooled, and the solid which separated was collected and washed with ethanol to give 8.6 g. of 4,5-dibromopyrrole-2-carboxylic acid salicylidenehydrazide, m.p. 265°-266° C. (dec.).

By replacing the salicylaldehyde used in the above-described procedure with a molar equivalent amount of benzaldehyde, there can be obtained 4,5-dibromopyrrole-2-carboxylic acid benzylidenehydrazide.

EXAMPLE 31

4,5-Dichloropyrrole-2-carboxylic acid (10 g., 0.05 mole) was converted to the corresponding acid chloride by reaction with 15 ml. of thionyl chloride and the acid chloride dissolved in 25 ml. of benzene was reacted with 6.0 g. (0.05 mole) of 2-amino-6-methylpyridine in 75 ml. of pyridine using the procedure described above in Example 3. The product was recrystallized from dilute ethanol to give 1.7 g. of 4,5-dichloro-N-(6-methyl-2-pyridyl)pyrrole-2-carboxamide, m.p. 235°-236° C.

By replacing the 2-amino-6-methylpyridine used in the above-described procedure with a molar equivalent amount of 2-aminopyridine, there can be obtained 4,5-dichloro-N-(2-pyridyl)pyrrole-2-carboxamide.

EXAMPLE 32

4,5-Dibromopyrrole-2-carboxylic acid (16.5 g., 0.062 mole) was converted to the corresponding acid chloride by reaction with 25 ml. of thionyl chloride, and the acid chloride dissolved in 30 ml. of benzene was reacted with 6.2 g. (0.062 mole) of 2-aminothiazole in 65 ml. of pyridine using the procedure described above in Example 3. The product was recrystallized from a 6:3:1 dimethylformamide/ethanol/water mixture to give two crops totaling 14.6 g. of 4,5-dibromo-N-(2-thiazolyl)-pyrrole-2-carboxamide, m.p. 265°-266° C.

EXAMPLE 33

A mixture of 18.5 g. (0.05 mole) of 4,5-dibromopyrrol-2-yl trichloromethyl ketone (described above in Example 8) and 3.6 g. (0.025 mole) of 1,8-diaminooctane in 25 ml. of dimethylformamide was heated on a steam bath for about four hours, the mixture diluted with water, and the solid precipitate collected, dried, and recrystallized from ethyl acetate to give 12.1 g. of N,N'-octamethylene-bis-(4,5-dibromopyrrole-2-carboxamide), m.p. 210°-212° C.

By replacement of the 1,8-diaminooctane used in the above-described procedure with a molar equivalent amount of ethylenediamine, 1,4-butylenediamine, or 1,6-hexylenediamine, there can be obtained, respectively, N,N'-(1,2-ethylene)bis(4,5-dibromopyrrole-2-carboxamide); N,N'-(tetramethylene)bis(4,5-dibromopyrrole-2-carboxamide); or N,N'-(hexamethylene)bis(4,5-dibromopyrrole-2-carboxamide).

EXAMPLE 34

4,5-Dichloropyrrole-2-carboxylic acid chloride (11.6 g., 0.057 mole), prepared from 16 g. (0.057 mole) of 4,5-dichloropyrrol-2-yl trichloromethyl ketone using the procedure described above in Example 3, was treated with a solution of 10.3 g. (0.06 mole) of 2-chloro-4-nitroaniline in 100 ml. of pyridine using the procedure described above in Example 3. The crude product was recrystallized from aqueous dimethylformamide to give 4.6 g. of 2',4,5-trichloro-4'-nitro-pyrrole-2-carboxanilide, m.p. 294°-296° C.

BIOLOGICAL TEST RESULTS

Antibacterial data, expressed in terms of the minimum inhibitory concentration, obtained for the compounds of the invention are given below. The organism number refers to *Staphylococcus aureus*, *Pseudomonas aeruginosa*, *Escherichia coli* and *Proteus vulgaris*, respectively.

|         | Test Organism |       |       |       |
|---------|-------|-------|-------|-------|
| Example | 1     | 2     | 3     | 4     |
| 1       | 7.8   | >125  | 31.2  | >250  |
| 2       | 250   | >125  | >250  | >250  |
| 3       | 0.075 | >62.5 | >125  | >125  |
| 4       | 7.8   | >62.5 | >250  | >125  |
| 5       | 0.97  | >62.5 | >125  | >125  |
| 6       | 15.6  | >62.5 | >125  | >125  |
| 7       | 3.9   | >125  | 7.8   | >125  |
| 8       | 0.62  | 125   | 125   | >125  |
| 9       | 0.31  | 62.5  | 7.8   | 250   |
| 10      | 0.12  | >125  | 7.8   | 250   |
| 11      | 3.9   | 125   | >125  | >125  |
| 12      | 15.6  | >125  | 125   | >125  |
| 13      | 5     | >100  | >100  | >100  |
| 14      | 0.3   | >100  | >100  | >100  |
| 15      | 2.5   | >125  | >125  | >125  |
| 16      | >62.5 | 62.5  | >125  | >125  |
| 17      | >125  | >125  | >125  | >125  |
| 18      | >125  | >62.5 | >125  | >125  |
| 19      | >125  | >125  | >125  | >125  |
| 20      | >125  | 62.5  | 125   | >125  |
| 21      | >125  | >62.5 | >125  | >125  |
| 22      | 0.8   | >125  | >250  | 22 125|
| 23      | >62.5 | 62.5  | >62.5 | >62.5 |
| 24      | 31.2  | >125  | >250  | >250  |
| 25      | 31.2  | >125  | >250  | >250  |
| 27      | >250  | >125  | >250  | >250  |
| 28      | >250  | >125  | >250  | >250  |
| 29      | 31.2  | >125  | 125   | >250  |
| 30      | 31.2  | >62.5 | 62.5  | 125   |
| 31      | >125  | >62.5 | >125  | >125  |
| 32      | >125  | >62.5 | >125  | >125  |
| 33      | 250   | >125  | >125  | >125  |

Post emergence herbicidal test data, expressed in terms of the vigor rating scale described above and the percent kill, are given below. The plant test species used (lima bean, corn, lettuce, mustard and crabgrass) are identified by the letters A, B, C, D and E, respectively.

|     | Test species |       |       |       |       |       |       |       |       |       |
|-----|--------------|-------|-------|-------|-------|-------|-------|-------|-------|-------|
|     | A            |       | B     |       | C     |       | D     |       | E     |       |
| Ex. | Vigor | %Kill | Vigor | %Kill | Vigor | %Kill | Vigor | %Kill | Vigor | %Kill |
|     | 5 | 0 | 5 | 0 | 3 | 40 | 5 | 0 | 4 | 0 |
| 3   | 4 | 0 | 5 | 0 | 2 | 80 | 4 | 0 | 4 | 0 |
| 5   | 4 | 0 | 5 | 0 | 1 | 90 | 5 | 0 | 5 | 0 |
| 6   | 5 | 0 | 5 | 0 | 3 | 40 | 4 | 0 | 5 | 0 |
| 7   | 5 | 0 | 5 | 0 | 3 | 80 | 3 | 40 | 5 | 0 |
| 9   | 5 | 0 | 5 | 0 | 1 | 90 | 5 | 0 | 5 | 0 |
| 16  | 4 | 0 | 5 | 0 | 2 | 80 | 2 | 80 | 1 | 90 |
| 24  | 4 | 0 | 5 | 0 | 3 | 80 | 5 | 0 | 5 | 0 |
| 25  | 5 | 0 | 5 | 0 | 4 | 0  | 3 | 80 | 5 | 0 |
| 28  | 5 | 0 | 5 | 0 | 3 | 60 | 5 | 0 | 5 | 0 |

The above results show that each of the species listed has postemergence activity against lettuce, a broad leaf plant, while certain species, those of Examples 7, 16 and 25, are active against mustard, another broad leaf plant. One species, the compound of Example 16, is also active against crabgrass.

The compound of Example 25 also was found to have preemergence herbicidal activity against crabgrass, but not other plant test species, in that although none of the test crabgrass plants had been completely killed at the end of the test period, the compound proved so injurious to them that they could not recover. Data on the compound, expressed in terms of the vigor rating and percent kill, are as follows:

|  | Vigor | %Kill |
|---|---|---|
| Lima Bean | 3 | 0 |
| Corn | 3 | 0 |
| Lettuce | 5 | 0 |
| Mustard | 3 | 0 |
| Crabgrass | 1 | 0 |

I claim:
1. A compound having the formula:

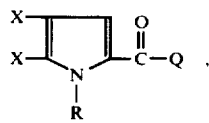

wherein X is chlorine, bromine or iodine, both values of X being identical; R is hydrogen or lower-alkyl; and Q is a member of the group consisting of benzylamino, hydrazino, phenylamino or phenylamino substituted in the phenyl ring by from one to two lower-alkoxy, halogen, lower-alkyl, trifluoromethyl, nitro or sulfamoyl groups.

2. A compound having the formula

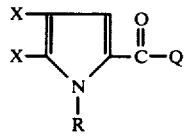

wherein X is chlorine, bromine or iodine, both values of X being identical; R is hydrogen or lower-alkyl; and Q is phenylamino or phenylamino substituted in the phenyl ring by from one to two lower-alkoxy, halogen, lower-alkyl, trifluoromethyl, nitro or sulfamoyl groups.

3. A compound according to claim 1 wherein R is hydrogen and Q is benzylamino.

4. A compound according to claim 1 wherein R is hydrogen and Q is hydrazino.

5. 4,5-Dichloropyrrole-2-carboxanilide according to claim 2.

6. 3',4,5,5'-Tetrachloropyrrole-2-carboxanilide according to claim 2.

7. 3',4,5-Trichloropyrrole-2-carboxanilide according to claim 2.

8. 4,4',5-Trichloropyrrole-2-carboxanilide according to claim 2.

9. 4,5-Dichloro-4'-methylpyrrole-2-carboxanilide according to claim 2.

10. 4,5-Dichloro-4'-fluoropyrrole-2-carboxanilide according to claim 2.

11. 3',4,5-Tribromopyrrole-2-carboxanilide according to claim 2.

12. 4,4',5-Tribromopyrrole-2-carboxanilide according to claim 2.

13. 4,5-Dibromo-4'-chloropyrrole-2-carboxanilide according to claim 2.

14. 3',4,4',5-Tetrachloropyrrole-2-carboxanilide according to claim 2.

15. 2',4,5,6'-Tetrachloropyrrole-2-carboxanilide according to claim 2.

16. 4,5-Dibromo-3',5'-dichloropyrrole-2-carboxanilide according to claim 2.

17. 4,5-Dibromo-3',5'-bis(trifluoromethyl)pyrrole-2-carboxanilide according to claim 2.

18. 3',4,5,5'-Tetrabromopyrrole-2-carboxanilide according to claim 2.

19. 2',4,4',5-Tetrachloropyrrole-2-carboxanilide according to claim 2.

20. 3',5'-Dichloro-4,5-diiodopyrrole-2-carboxanilide according to claim 2.

21. N-Benzyl-4,5-dichloropyrrole-2-(N-benzylcarboxyamide) according to claim 3.

22. 4,5-Dibromopyrrole-2-carboxylic acid hydrazide according to claim 6.

* * * * *